(12) United States Patent
He et al.

(10) Patent No.: US 8,394,918 B2
(45) Date of Patent: Mar. 12, 2013

(54) FIVE-RING FUSED HETEROAROMATIC COMPOUNDS AND CONJUGATED POLYMERS THEREOF

(75) Inventors: Mingqian He, Horseheads, NY (US); Thomas Mark Leslie, Horseheads, NY (US); Weijun Niu, Painted Post, NY (US); Adama Tandia, Nelson, PA (US)

(73) Assignee: Corning Incorporated, Corning, NY (US)

( * ) Notice: Subject to any disclaimer, the term of this patent is extended or adjusted under 35 U.S.C. 154(b) by 45 days.

(21) Appl. No.: 13/036,269

(22) Filed: Feb. 28, 2011

(65) Prior Publication Data

US 2012/0220748 A1    Aug. 30, 2012

(51) Int. Cl.
*C08G 75/00* (2006.01)
(52) U.S. Cl. .................... 528/377; 528/380
(58) Field of Classification Search .......... 528/380, 528/377
See application file for complete search history.

(56) References Cited

U.S. PATENT DOCUMENTS

| | | | |
|---|---|---|---|
| 7,838,623 B2 | 11/2010 | He | 528/377 |
| 2005/0082525 A1 | 4/2005 | Heeney et al. | 257/40 |
| 2007/0161776 A1 | 7/2007 | He | 528/373 |
| 2007/0235726 A1 | 10/2007 | Li et al. | 257/40 |
| 2007/0260069 A1 | 11/2007 | Li et al. | 549/29 |

FOREIGN PATENT DOCUMENTS

| | | |
|---|---|---|
| EP | 1916250 | 4/2008 |
| JP | 2009-054810 | * 3/2009 |
| JP | 2009-54810 | 3/2009 |
| JP | 2011-233724 | 11/2011 |
| WO | 2006/031893 | 3/2006 |
| WO | 2008/106019 | 9/2008 |
| WO | 2009/123695 | 10/2009 |
| WO | 2010/000669 | 1/2010 |
| WO | 2010/000670 | 1/2010 |
| WO | 2010/000755 | 1/2010 |
| WO | 2010/018081 | 2/2010 |
| WO | 2010/061176 | 6/2010 |
| WO | 2011/010710 | 1/2011 |
| WO | 2011/158953 | 12/2011 |

OTHER PUBLICATIONS

Gao et al. (Advanced Materials, 2009, 21,213-216).*
Herbert, M., et al., "Preparation of 2,3-[2-Thienyl]Butane-2,3-Diol and 4,8-Dimethylbenzo[1,2-b;4,5-b']Dithiophene", Comptes Rendus des Seances de l'Academie des Sciences, Serie C: Sciences Chimiques (1971) 273(14), 825-8.

(Continued)

*Primary Examiner* — Shane Fang
(74) *Attorney, Agent, or Firm* — John L. Haack

(57) ABSTRACT

Compounds having a core comprised of an aromatic ring and at least two annulated beta-substituted fused thiophene ring systems of the general formula:

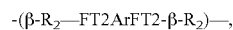

and polymers or copolymers thereof, of the general formulas:

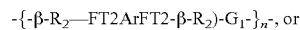

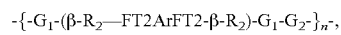

where $\beta$-$R_2$—FT2ArFT2-$\beta$-$R_2$, -$G_1$-, -$G_2$-, and n are as defined herein. Also disclosed are compositions, articles, or devices comprising the polymers, and methods for making and using the polymers. The compositions, articles, or devices can be used, for example, for electronic applications, such as light emitting devices and semiconductor devices.

2 Claims, 8 Drawing Sheets

OTHER PUBLICATIONS

Caullet, C., et al., Identification of a Product Obtained by the Electrochecmial Reduction of 2-Acetylthiophene in an Acid Medium in a Water-Tetrahydrofuran Mixture Comptes Rendus, Serie C: Sciences Chimiques, (1967), 264(2), 228-31.

Pan, H., et al., "Low Temperature, Solution-Processed, High-Mobility Polymer Semiconductors for Thin-Film Transistors", J. Amer. Chem. Soc., (2007) 129(14), 4112-4113.

Pan, H., et al., "Benzodithiophene Copolymer—A Low-Temperature, Solution-Processed High-Performance Semiconductor for Thin-Film Transistors", Advanced Functional Materials, (2007) 17(17), 35743579.

Fong, H.-H., et al., "Tetrathienoacene Copolymers as High Mobility, Soluble Organic Semiconductors", J. Am. Chem. Soc., (2008), 130(40), 13202-13203.

Sirringhaus, H., et al., Dibenzothienobisbenzothiophene a Noval Fused-Rig Oligomer With High Field-Effect Mobility, Journal of Materials Chemistry (1999), 9(9), 2095-2101.

Liu, M., et al., "A Polymer With a Benzo[2,1-B;3-4-b']Dithiophene Moiety FRO Photovoltaic Applications", ChemSusChem, (2010) 3(1), 106-111.

Reiger, R., et al., "Rational Optimization of Benzo[2,1b;3,4-b']Dithiophene-Containing Polymers for Organic Field-Effect Transistors", Advanced Materials (Weinheim, Germany) (2010) 22(1), 83-86, ISSN:0935-9648.

Anthony, J., "Functionalized Acenes and Heteroacenes for Organic Electronics", Chemical Reviews (US), (2006), 106(12), 5028-5048.

* cited by examiner

Fig. 1 [prior art]
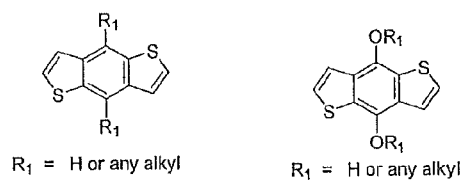
R₁ = H or any alkyl  R₁ = H or any alkyl
Fig. 2 [prior art]
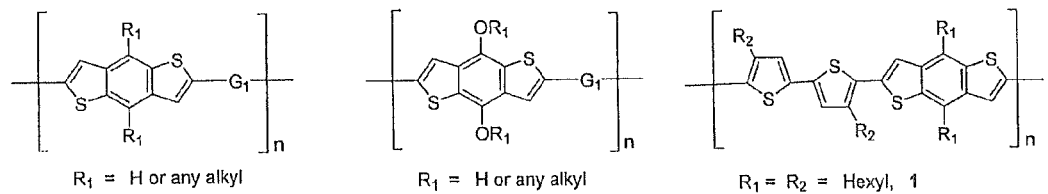
R₁ = H or any alkyl  R₁ = H or any alkyl  R₁ = R₂ = Hexyl, 1
Fig. 3 [prior art]
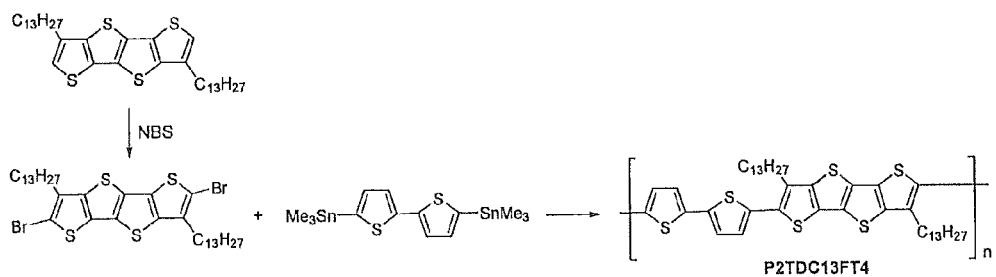

Fig. 5 [prior art]
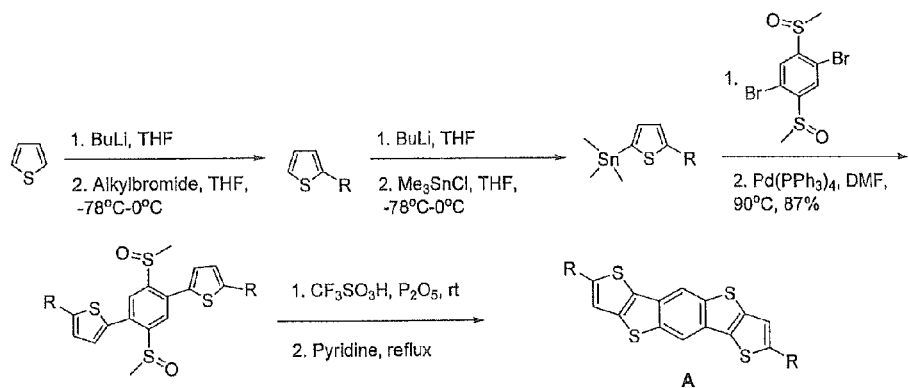
Fig.6
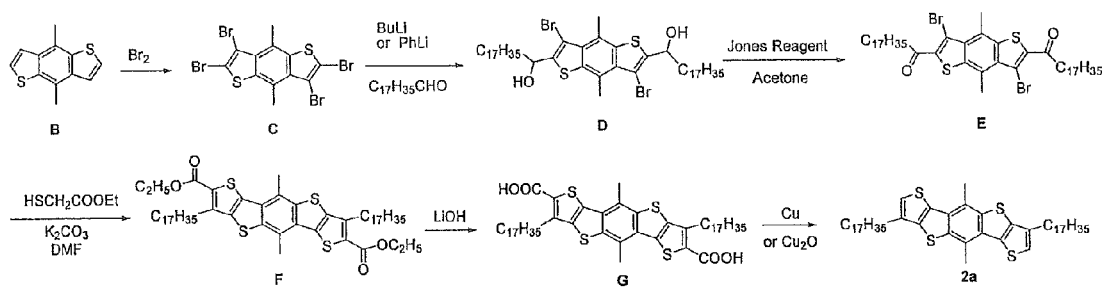

Fig. 7
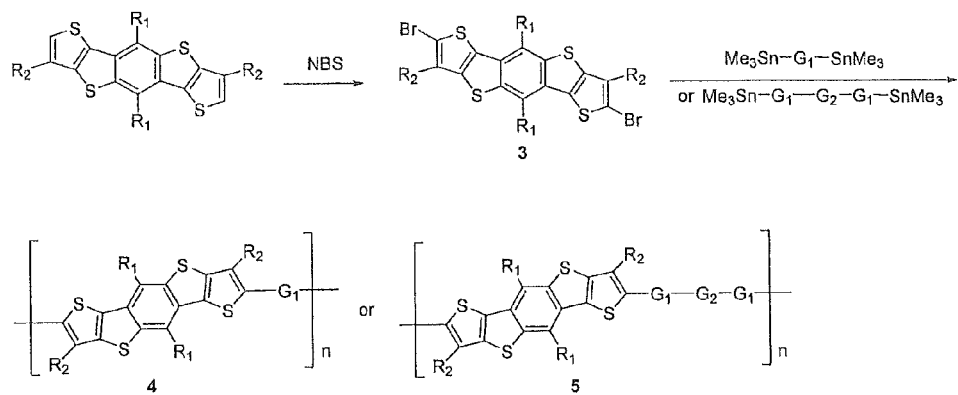
$Me_3Sn-G_1-SnMe_3$ or $Me_3Sn-G_1-G_2-G_1-SnMe_3$ can be, for example,
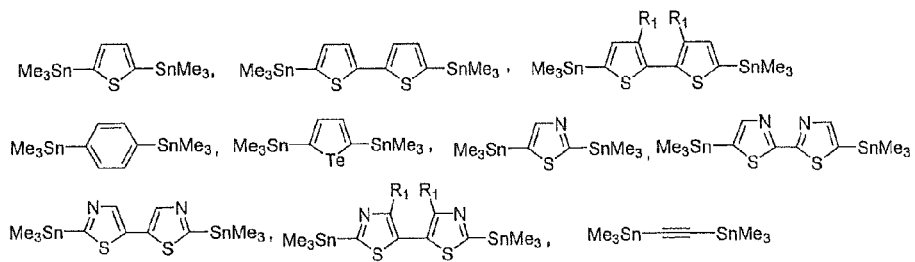
Fig. 8
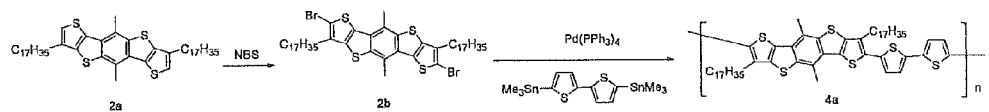

Fig. 14
Table 1.
| | |
|---|---|
| 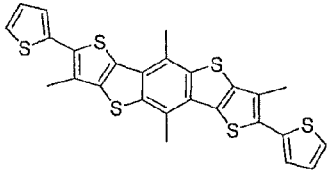 | Hole Reorg E (eV): 0.199<br>Model Compound: 9 |
| 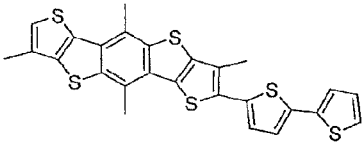 | Hole Reorg E (eV): 0.207<br>Model Compound: 10 |
| 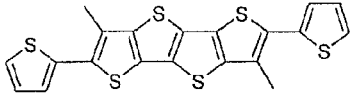 | Hole Reorg E (eV): 0.243<br>Model Compound: 19 |

FIVE-RING FUSED HETEROAROMATIC COMPOUNDS AND CONJUGATED POLYMERS THEREOF

The entire disclosure of any publication or patent document mentioned herein is incorporated by reference.

BACKGROUND

The disclosure generally relates to compounds and polymers having a core comprised of an aromatic ring and annulated fused thiophenes, to compositions, to articles, and to methods for making and using the compounds and polymers.

SUMMARY

The disclosure provides compounds and polymers having a five-ring fused heteroaromatic core comprised of an aromatic ring and annulated beta-substituted fused thiophenes, to compositions, to articles, and to methods for making and using compounds and polymers that can be used, for example, for electronic applications, such as light emitting devices and semiconductor devices, and methods of making and using the compounds and polymers.

BRIEF DESCRIPTION OF DRAWINGS

In embodiments of the disclosure:

FIG. 1 shows known examples of substituted and unsubstituted three-ring fused heteroaromatics related to the disclosure.

FIG. 2 shows known examples of semiconductor polymers incorporating the three-ring fused heteroaromatics of FIG. 1.

FIG. 3 shows an example of Applicant's prior high performance semiconductor polymer P2TDC13FT4 and a partial synthetic route.

FIG. 5 shows an example of a known route to an α-, α'-alkyl substituted five-ring fused ring heteroaromatic compound of the formula A.

FIG. 6 shows an example route to α-, α'-unsubstituted, β-, β'-alkyl substituted five-ring fused ring heteroaromatics of formula 2a.

FIG. 7 shows an example of a route to semiconducting polymers of formulas 4 and 5 containing α-, α'-aromatic ring substituted, β-, β'-alkyl substituted five-ring fused ring heteroaromatic cores.

FIG. 8 shows an example of a route to a semiconducting polymer of the formula 4a.

FIG. 9 shows an example of an unsuccessful synthesis of an α-, α'-alkyl substituted five-ring fused ring heteroaromatic of the formula 3a.

FIG. 14 provides Table 1 that lists Hole Reorganization Energies obtained from modeling for selected fused core model compounds.

DETAILED DESCRIPTION

Figure 4:
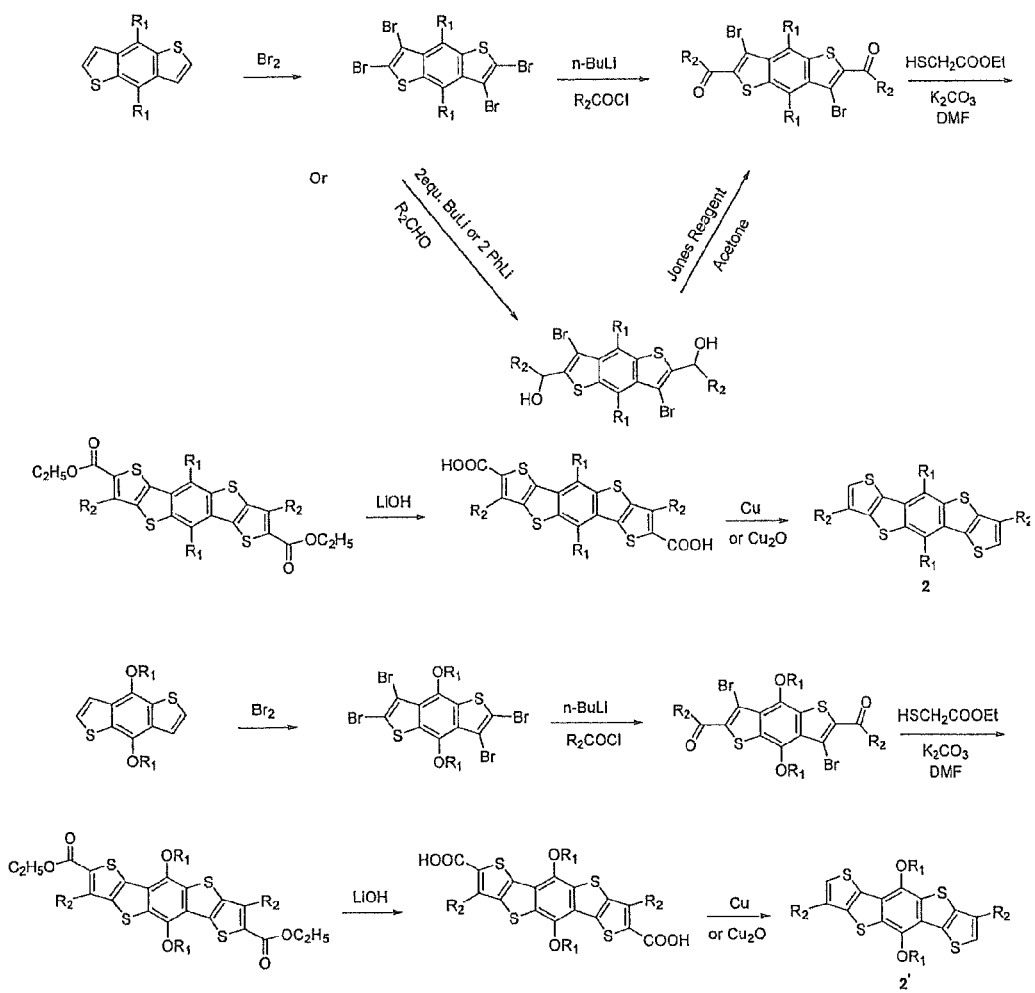
FIG. 4 shows example syntheses of a class of α-, α'-unsubstituted, β, β'-alkyl substituted five-ring fused ring heteroaromatics of the formula 2 and 2'.

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments for the claimed invention.

DEFINITIONS

"Unit," "polymerizable unit," or like terms in the context of the disclosed polymers or copolymers refer to the number of different core units and like other conjugated units within a discrete repeat segment (n) of a polymer or copolymer, see for example the core unit having a core comprised of a central aryl or aromatic ring (Ar) and at least two oppositely situated annulated beta-substituted fused thiophenes (β-$R_2$—FT2) of the general representation β-$R_2$—FT2ArFT2-β-$R_2$, and at least one non-fused backbone aryl or heteroaryl unit(s), -(Ar)$_m$-, where m is from 1 to about 6, comprised of, for example, one or more -$G_1$-, -$G_2$-, or -$G_1$-$G_2$-$G_1$-, and combinations thereof, such as polymers or copolymers of the general formulas:

-{-(core)-(Ar)$_m$-}$_n$ or

-{-β'-$R_2$—FT2ArFT2-β-$R_2$)-(Ar)$_m$-}$_n$, such as

-{-(β-$R_2$—FT2ArFT2-β-$R_2$)-$G_1$-}$_n$-, and

-{-$G_1$-β-$R_2$—FT2ArFT2-β-$R_2$)-$G_1$-$G_2$-}$_n$—, or

-{-(β-$R_2$—FT2ArFT2-β-$R_2$)-$G_1G_2G_1$-}$_n$-.

In embodiments, a repeat unit or segment (n) can have one or more like core units and one or more additional conjugated units (i.e., $G_1$, -$G_1$-$G_2$-) within a discrete repeat segment of a polymer.

"Hydrocarbon," "hydrocarbyl," "hydrocarbylene," "hydrocarbyloxy," and like terms refer to monovalent such as —R, or divalent —R— moieties, and can include, for example, alkyl hydrocarbons, aromatic or aryl hydrocarbons, alkyl substituted aryl hydrocarbons, alkoxy substituted aryl hydrocarbons, heteroalkyl hydrocarbons, heteroaromatic or heteroaryl hydrocarbons, alkyl substituted heteroaryl hydrocarbons, alkoxy substituted heteroaryl hydrocarbons, and like hydrocarbon moieties, and as illustrated herein.

"Alkyl" includes linear alkyls, branched alkyls, and cycloalkyls. "Substituted alkyl" or "optionally substituted alkyl" refers to an alkyl substituent, which can include, for example, a linear alkyl, a branched alkyl, or a cycloalkyl, having from 1 to 4 optional substituents selected from, for example, hydroxyl (—OH), halogen, amino (—$NH_2$ or —$NR_2$), nitro (—$NO_2$), acyl (—C(=O)R), alkylsulfonyl (—S(=O)$_2$R), alkoxy (—OR), and like substituents, where R of the optional substituent can be a hydrocarbyl, aryl, Het, or like moieties, such as a monovalent alkyl or a divalent alkylene having from 1 to about 10 carbon atoms. For example, a hydroxy substituted alkyl, can be a 2-hydroxy substituted propylene of the formula —CH$_2$—CH(OH)—CH$_2$—, an alkoxy substituted alkyl, can be a 2-methoxy substituted ethyl of the formula —CH$_2$—CH$_2$-β-CH$_3$, an amino substituted alkyl, can be a 1-dialkylamino substituted ethyl of the formula —CH(NR$_2$)—CH$_3$, an oligo-(oxyalkylene), poly-(oxyalkylene), or poly-(alkylene oxide) substituted alkyl, can be, for example, of the partial formula —(R—O)$_x$—, where x can be, for example, from 1 to about 50, and from 1 to about 20, and like substituted oxyalkylene substituents, such as of the formula —(CR$^5$—CHR$^5$—O)$_x$— where R$^5$ is hydrogen or a substituted or unsubstituted (C$_{1-8}$) hydrocarbyl such as alkyl, and x is an integer of from 1 to about 50.

"Aryl" includes a mono- or divalent-phenyl radical, or an ortho-fused bicyclic carbocyclic radical having about nine to twenty ring atoms in which at least one ring is aromatic. Aryl (Ar) can include substituted aryls, such as a phenyl radical having from 1 to 5 substituents, for example, alkyl, alkoxy, halo, and like substituents. An "Aryl" core includes a substituted or unsubstituted (i.e., in the 1- and 4-positions, while the 2,3- and 5,6-positions are, respectively, heteroaryl substituents such the FT2 groups), bis-annulated, bis-ortho-fused phenyl radical, or an ortho-fused bicyclic carbocyclic radical having about nine to twenty ring atoms in which at least one ring is aromatic. Aryl (Ar) substituents or cores can include substituted or unsubstituted, heteroaryls or heterocyclics.

"Het" includes a four-(4), five-(5), six-(6), or seven-(7) membered saturated or unsaturated heterocyclic ring having 1, 2, 3, or 4 heteroatoms selected from the group consisting of oxy, thio, sulfonyl, sulfonyl, selenium, tellurium, and nitrogen, which ring is optionally fused to a benzene ring. Het also includes "heteroaryl," which encompasses a radical attached via a ring carbon of a monocyclic aromatic ring containing five or six ring atoms consisting of carbon and 1, 2, 3, or 4 heteroatoms each selected from the group consisting of non-peroxide oxy, thio, and N(X) wherein X is absent or is H, O, (C$_{1-4}$)alkyl, phenyl, or benzyl, and a radical of an ortho-fused bicyclic heterocycle of about eight to ten ring atoms derived therefrom, particularly a benzo-derivative or one derived by fusing a propylene, trimethylene, or tetramethylene diradical thereto. A particularly useful Aryl (Ar) backbone moiety includes substituted or unsubstituted, divalent thiophene.

In embodiments, halo or halide includes fluoro, chloro, bromo, or iodo. Alkyl, alkoxy, etc., include both straight and branched groups; but reference to an individual radical such as "propyl" embraces only the straight chain radical, a branched chain isomer such as "isopropyl" being specifically referred to.

The carbon atom content of various hydrocarbon-containing (i.e., hydrocarbyl) moieties can alternatively be indicated by a prefix designating a lower and upper number of carbon atoms in the moiety, i.e., the prefix indicates a moiety of the integer "i" to the integer "j" carbon atoms, inclusive. Thus, for example, C$_1$ to C$_8$ alkyl, (C$_1$-C$_8$)alkyl, or C$_{1-8}$alkyl refers to an alkyl of one to eight carbon atoms, inclusive, and hydrocarbyloxy such as (C$_1$-C$_8$)alkoxy or C$_{1-8}$alkoxy refers to an alkoxy radical (—OR) having an alkyl group of one to eight carbon atoms, inclusive. In another example, C$_1$ to C$_{40}$ alkyl, (C$_1$-C$_{40}$)alkyl, (C$_{1-40}$) alkyl, or C$_{1-40}$alkyl refers to an alkyl of one to forty carbon atoms, inclusive, and hydrocarbyloxy such as (C$_1$-C$_{40}$)alkoxy or C$_{1-40}$alkoxy refers to an alkoxy radical (—OR) having an alkyl group of one to forty carbon atoms, inclusive.

Specifically, C$_{1-8}$alkyl can be, for example, methyl, ethyl, propyl, isopropyl, butyl, iso-butyl, sec-butyl, tert-butyl, pentyl, 3-pentyl, hexyl, heptyl, or octyl; (C$_{3-12}$)cycloalkyl can be cyclopropyl, cyclobutyl, cyclopentyl, cyclohexyl, cycloheptyl, cyclooctyl, etc., including bicyclic, tricyclic, or multicyclic substituents, and like substituents.

A specific "hydrocarbyl" can be, for example, (C$_{1-40}$)hydrocarbyl, including all intermediate chain lengths and values. Preferred "hydrocarbyl" groups can be, for example, those R$_1$ and R$_2$ groups which can impart enhanced solubility to the monomer or co-monomer starting materials, or to the resulting polymers, such as (C$_{16}$)hydrocarbyl, (C$_{17}$)hydrocarbyl, (C$_{18}$)hydrocarbyl, (C$_{20}$)hydrocarbyl, (C$_{22}$)hydrocarbyl, (C$_{24}$)hydrocarbyl, (C$_{26}$)hydrocarbyl, (C$_{28}$)hydrocarbyl, (C$_{30}$)hydrocarbyl, (C$_{32}$)hydrocarbyl, (C$_{34}$)hydrocarbyl, (C$_{36}$)hydrocarbyl, (C$_{38}$)hydrocarbyl, (C$_{40}$)hydrocarbyl, including all intermediate chain lengths and values, and mixtures thereof, for example, (C$_{16-40}$)hydrocarbyl, (C$_{20-40}$)hydrocarbyl, (C$_{22-36}$)hydrocarbyl, (C$_{22-40}$)hydrocarbyl, and (C$_{26-40}$)hydrocarbyl, (C$_{30-40}$)hydrocarbyl.

C$_{1-8}$alkoxy can be, for example, methoxy, ethoxy, propoxy, isopropoxy, butoxy, iso-butoxy, sec-butoxy, pentoxy, 3-pentoxy, hexyloxy, 1-methylhexyloxy, heptyloxy, octyloxy, and like substituents.

H—C(═O)(C$_{3-7}$)alkyl- or —(C$_{2-7}$)alkanoyl can be, for example, acetyl, propanoyl, butanoyl, pentanoyl, 4-methylpentanoyl, hexanoyl, or heptanoyl. Aryl (Ar) can be, for example, phenyl, naphthyl, anthracenyl, phenanthrenyl, fluorenyl, tetrahydronaphthyl, or indanyl. Het can be, for example, pyrrolidinyl, piperidinyl, morpholinyl, thiomorpholinyl, or heteroaryl. Heteroaryl can be, for example, furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), or quinolyl (or its N-oxide).

A specific value for Het includes a five-(5), six-(6), or seven-(7) membered saturated or unsaturated ring containing 1, 2, 3, or 4 heteroatoms, for example, non-peroxide oxy, thio, sulfinyl, sulfonyl, selenium, tellurium, and nitrogen; and a radical of an ortho-fused bicyclic heterocycle of about eight to twelve ring atoms derived therefrom, particularly a benzo-derivative or one derived by fusing a propylene, trimethylene, tetramethylene, or another monocyclic Het diradical thereto.

Other conditions suitable for formation and modification of the compounds, oligomers, polymers, composites or like products of the disclosure, from a variety of starting materials or intermediates, as disclosed and illustrated herein, are available. For example, see Feiser and Feiser, "Reagents for Organic Synthesis", Vol. 1, et seq., 1967; March, J. "Advanced Organic Chemistry," John Wiley & Sons, 4$^{th}$ ed. 1992; House, H. O., "Modem Synthetic Reactions," 2$^{nd}$ ed., W. A. Benjamin, New York, 1972; and Larock, R. C., "Comprehensive Organic Transformations," 2$^{nd}$ ed., 1999, Wiley-VCH Publishers, New York. The starting materials employed in the preparative methods described herein are, for example, commercially available, have been reported in the scientific literature, or can be prepared from readily available starting materials using procedures known in the field or provided in the working examples. It may be desirable to optionally use a protecting group during all or portions of the above described or alternative preparative procedures. Such protecting groups and methods for their introduction and removal are known in the art. See Greene, T. W.; Wutz, P. G. M. "Protecting Groups In Organic Synthesis," 2$^{nd}$ ed., 1991, New York, John Wiley & Sons, Inc.

"Include," "includes," or like terms means encompassing but not limited to, that is, inclusive and not exclusive.

"Monomer," "mer," or like terms refer to a compound that can be (or has already been) covalently combined or linked with other monomers of like or different structure to form homogenous (homopolymers) or heterogeneous (e.g., copolymers, terpolymers, and like heteropolymers) chains of the target polymer. "Polymer" or like terms includes copolymers. Suitable monomers as disclosed and illustrated herein can include, for example, low molecular weight polymerizable compounds, such as from about 50 to about 200 Daltons, and higher molecular weight compounds, such as from about 200 to about 10,000 Daltons, including divalent or bifunctionally reactive compounds as disclosed herein, such as di-tin fused thiophene compounds, di-halogen thiophene compounds, di-halogen oligo-thiophene compounds, and like compounds.

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example: through typical measuring and handling procedures used for making compounds, compositions, composites, concentrates or use formulations; through inadvertent error in these procedures; through differences in the manufacture, source, or purity of starting materials or ingredients used to carry out the methods; expressing measured polymer number average or weight average molecular weight properties, and like considerations. The term "about" also encompasses amounts that differ due to aging of a composition or formulation with a particular initial concentration or mixture, and amounts that differ due to mixing or processing a composition or formulation with a particular initial concentration or mixture. The claims appended hereto include equivalents of these "about" quantities.

"Consisting essentially of" in embodiments refers, for example, to a compound, to a polymer or copolymer composition, to a method of making or using the compound, the polymer, the copolymer, a formulation, or composition, and articles, devices, or any apparatus of the disclosure, and can include the components or steps listed in the claim, plus other components or steps that do not materially affect the basic and novel properties of the compositions, articles, apparatus, or methods of making and use of the disclosure, such as particular reactants, particular additives or ingredients, a particular agent, a particular monomer, co-monomer, or condition, or like structure, material, or process variable selected. Items that may materially affect the basic properties of the components or steps of the disclosure or that may impart undesirable characteristics to the present disclosure include, for example, premature polymer chain termination, excessive crosslinking, extended or unnecessary exposure of the resulting polymer to excessively high temperatures, and like contrary steps.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

Specific and preferred values disclosed for components, reactants, reagents, ingredients, additives, initiators, metal catalysts, cross linkers, and like aspects, and ranges thereof, are for illustration only; they do not exclude other defined values or other values within defined ranges. The compositions and methods of the disclosure include those having any value or any combination of the values, specific values, more specific values, and preferred values described herein. Any aspect, feature, or embodiment recited in the appended claims can be used in any combination or permutation with any one or more other aspect, feature, or embodiment recited in the appended claims.

Organic semiconducting compounds (OSC), including oligomers and polymers, have been the focus of academic and industrial research because of their interesting electronic and optoelectronic properties. These organic materials have a variety of applications including organic thin film transistors (OTFTs), organic light-emitting diodes (OLEDs), and electro-optic (EO) applications. Fused aromatics and their oligomeric and polymeric derivatives have been widely used as valuable organic thin film transistors due to their good pi-stacking in the solid state, good thermal stability, and high device performance. Although three-ring fused hetero-aromatics having a middle phenyl ring and two external thiophene rings (FIG. 1) were discovered more than 30 years ago (see Hebert, M., et al., Preparation of 2,3-[di(2-thienyl) butane-2,3-diol and 4,8-dimethylbenzo[1,2-b; 4,5,-b'] dithiophene," *Comptes Rendus des Seances de l'Academie des Sciences, Serie C: Sciences Chimiques* (1971), 273(14), 825-8; Caullet, C., et al., "Identification of a product obtained by the electrochemical reduction of 2-acetylthiophene in an acid medium in a water-tetrahydrofuran mixture," *Comptes Rendus, Serie C: Sciences Chimiques*, (1967), 264(2), 228-31), only recently have they been used as the repeat unit in semiconductor polymers (FIG. 2) (see for example, Pan, H., et al., "Low-Temperature, Solution-Processed, High-Mobility Polymer Semiconductors for Thin-Film Transistors," *J. Am. Chem. Soc.*, (2007), 129(14), 4112-4113; Ong, B., et al., "Electronic devices comprising poly(dithienyl-benzodithiophenes) as semiconductors," EP 1916250; Pan, H., et al., "Benzodithiophene copolymer—a low-temperature, solution-processed high-performance semiconductor for thin-film transistors," *Advanced Functional Materials*, (2007) 17(17), 3574-3579; Li, Y., et al., "Functionalized heteroacenes and polymers," U.S. Pat. Appl. Publ. US 2007260069; Li, Y., et al., "Poly[bis(ethynyl)heteroacene]s and electronic devices generated therefrom," U.S. Pat. Appl. Publ. US 2007235726; and Heeney, M., et al., "Polybenzodithiophenes useful for semiconductors or charge transport materials in optical, electro-optical or electronic devices," U.S. Pat. Appl. Publ. US 2005082525). These high performance semiconducting polymers 1 have a field-effect mobility larger than $0.1 \cdot cm^2/V \cdot s$. Comparison of published research results also indicated that fewer aromatic protons in the semiconductor polymers provided greater thermal stability to the polymers. Our previous high performance fused thiophene polymers (prepared as shown in FIG. 3) have high thermal stability in air due to the absence of aromatic protons in their fused thiophene ring core (see also Fong, H.-H., et al., "Tetrathienoacene Copolymers As High Mobility, Soluble Organic Semiconductors," *J. Am. Chem. Soc.*, (2008), 130 (40), 13202-13203).

In embodiments, the disclosure provides a group of α-, α'-un-substituted five-ring fused heteroaromatic compounds, including small molecules, oligomers, and polymers thereof, having a central phenyl ring and a total of four fused or annulated thiophene rings to provide a class of compounds having the general core structure of formula 2 or 2' in FIG. 4.

In embodiments, the disclosure also provides a synthetic method to make the aforementioned α-, α'-un-substituted five-ring fused hetero-aromatic compounds having the general core structure of formula 2 also shown in FIG. 4.

A recent publication described the synthesis of α-, α'-alkyl (or aryl) substituted five-ring fused heteroaromatics having compounds with a core structure of the formula A in FIG. 5 (see Kastler, M., et al. "High performance solution processible semiconductor based on dithieno[2,3-d:2',3'-d']benzo[1,2-b:4,5-b']dithiophene," WO 2010000670). The last step of ring closure to form the targeted five-ring fused hetero aromatic in FIG. 5 provided yields of 26% to 43% even though the α-position of thiophene was protected by an alkyl side chain. One complication in this last step is the possibility of intermolecular polymerization (see Sirringhaus, H., et al., "Dibenzothienobisbenzothiophene a novel fused-ring oligomer with high field-effect mobility," *Journal of Materials Chemistry* (1999), 9(9), 2095-2101).

Recently, there has been an interest in synthesizing semiconductor polymers for organic electronic applications (see for example, Kastler, M., et al., Polybenzothiophene polymers and process for their preparation and their use as semiconductors or charge transport materials," WO 2010018081; Liu, M., et al., "A Polymer with a Benzo[2,1-b; 3,4-b'] dithiophene Moiety for Photovoltaic Applications," *ChemSusChem*, (2010), 3(1),106-111; Kastler, M., et al., "Poly(5, 5'-bis(thiophen-2-yl)-benzo[2,1-b; 3,4-b']dithiophene) and its use as high performance solution processible semiconducting polymer," WO 2010000669; Kastler, M., et al., "Solution-processible semiconducting donor-acceptor copolymers," WO 2010000755; Rieger, R., et al., "Rational Optimization of Benzo[2,1-b; 3,4-b']dithiophene-Containing Polymers for Organic Field-Effect Transistors," *Advanced Materials* (Weinheim, Germany) (2010), 22(1), 83-86, ISSN: 0935-9648).

In embodiments, the disclosure provides compounds, polymer compositions, articles, and methods for making and using the compounds and polymers having a core having an aromatic center and annulated fused thiophenes.

In embodiments, the disclosure provides a compound having an aromatic center and at least two annulated fused thiophenes on opposite sides of the center, and a method of making the compounds as defined herein.

In embodiments, the disclosure provides a polymer or copolymer composition having a core comprising an aromatic center and at least two annulated fused thiophenes, and further comprising one or more aromatic or heteroaromatic substituent (such as -$G_1$- or -$G_1$-$G_2$-$G_1$-) situated between an adjacent core.

In embodiments, the disclosure provides articles having polymer or copolymer compositions having an aromatic center and annulated fused thiophenes.

In embodiments, the disclosure provides a polymeric or copolymeric composition, and articles thereof prepared by any of the processes as defined herein.

In embodiments, the disclosure provides an article or device incorporating the polymer, copolymeric, or polymer article as defined herein.

The disclosed compositions, articles, and methods can be used to prepare many different electro-optical devices, for example, OLEDs, OFETs, OTFTs, and like devices as disclosed, for example, in *J. Am. Chem. Soc.*, 2008, 130, 13202-13203.

In embodiments, the disclosure provides α-, α'-un-substituted five-ring fused heteroaromatic compounds having a core structure as embodied, for example, in the compound of formula 2 and 2' in FIG. 4 and synthetic methods for making the compounds. The three ring core starting materials and their polymers are known (see Hebert, M., et al., Preparation of 2,3-[di(2-thienyl)butane-2,3-diol and 4,8-dimethylbenzo[1,2-b; 4,5,-b']dithiophene," *Comptes Rendus* (1971), supra.).

In embodiments, the present disclosure provides methods for making the compound of formula 2a in FIG. 6 of this class of α-, α'-un-substituted five-ring fused heteroaromatic compounds. With such heteroaromatic compounds available having the general structure of formula 2, the preparation of the semiconductor polymers having monomers or co-monomers of the general structure of formula 4 and 5 as shown in FIG. 7 are also disclosed and demonstrated. The synthesis and characterization of this type of semiconductor polymer, for example, of the structure of formula 4a in FIG. 8 is demonstrated.

In embodiments, the disclosure also provides organic semiconducting polymers containing a fused aromatic repeat unit, for example, compounds of the formula 4 and 5 in FIG. 7.

In embodiments, the disclosure also provides methods for making the compound of formula 2a of this α-, α'-un-substituted five-ring fused heteroaromatic as shown in FIG. 6. Compound 2a and its precursors were purified as described in the examples and characterized by $^1$H NMR data. Compound 2a was prepared as a result of molecular modeling studies which suggested a potentially high mobility compound. A long alkyl side chain ("DC17" R=$C_{17}H_{35}$) was selected for the purpose of providing superior crystal packing properties and to in turn increase mobility and to provide superior solubility for correspondingly superior solution processing, such as purification, printing, and device fabrication applications. Adapting the known (see commonly owned and assigned U.S. Pat. No. 7,838,623, issued Nov. 23, 2010) synthetic procedure used to make the P2TDC13FT4 polymer illustrated in FIG. 3, the synthesis and characterization of the first example of this type of semiconductor polymer, such as the polymer of formula 4a in FIG. 8 were demonstrated. These organic semiconductor polymer materials having a $C_2$ symmetric repeat unit as shown in FIG. 7 have applications in, for example, organic electronics. Molecular modeling predicted that the polymer of the formula 4a in FIG. 8 should have superior mobility compared to our prior high performance polymer, P2TDCXFT4, as discussed below. Solution and solid UV-vis spectral data of the polymer of the formula 4a indicated that this is a likely high performance OTFT candidate.

The disclosed compounds, polymers, and preparative methods continue our development effort in organic semiconductor materials and provide numerous preparative and performance advantages (see He, M., "Preparation of fused thiophenes," WO 2006031893; He, M., "Fused thiophenes, methods for making fused thiophenes, and uses thereof," U.S. Pat. Appl. Publ. US 2007161776; He, M., "Fused thiophene monomers, oligomers and polymers for use in electronic devices," WO 2008106019; and He, M., "Fused thiophenes, methods for production and use in electronic devices," WO 2009123695). Compared to our prior four-ring fused thiophene small molecules (see commonly owned and assigned U.S. Pat. No. 7,838,623, issued Nov. 23, 2010), the existence of an additional phenyl ring in this class of α-, α'-un-substituted five-ring fused heteroaromatics having a core structure of the formula 2 in FIG. 4 extends the conjugation and may increase device performance. Comparison of small molecule organic electronic components indicates, in general, that a greater number of fused phenyl rings in similar structures increases mobility. The fused thiophene polymers disclosed in commonly owned and assigned WO2008/106019 (supra.) were synthesized by Stille coupling between a dibromo fused thiophene monomer and a di-tin non-fused aromatic monomer (or a vinyl di-tin monomer). Some advantages of the disclosed compounds, polymers, and preparative methods are discussed below.

Similar to our prior high performance β-, β'-alkyl substituted fused thiophene polymers (FT4-FT7 polymers) (see Fong, H. H., "Tetrathienoacene Copolymers As High Mobility, Soluble Organic Semiconductors," *J. Am. Chem. Soc.*, (2008), 130(40), 13202-13203), a $C_2$ symmetric repeat unit semiconductor polymer containing these α-, α'-un-substituted five-ring fused heteroaromatics as shown in FIG. 7 are predicted, using modeling, to have high device performance, yet they will probably provide different electronic properties due to the existence of the center fused phenyl ring.

Using the method shown in FIG. 4, synthesis of these α-, α'-un-substituted five-ring fused heteroaromatics was achieved. The first member of this α-, α'-un-substituted five-ring fused hetero-aromatics, compound (2a), was synthesized by this method and was purified and characterized as shown in FIG. 6. Compound 2a is expected to have higher mobility than that of DC17FT4 since published examples indicate that the substitution of thiophene rings by phenyl rings in fused aromatics increases mobility significantly (Anthony, J., "Functionalized acenes and heteroacenes for organic electronics," *Chemical Reviews* (US), (2006), 106(12), 5028-5048). This is consistent with our modeling data.

Semiconductor polymers containing these α-, α'-un-substituted five-ring fused heteroaromatics in FIG. 7 can be synthesized following our prior method to make the high performance β-, β'-alkyl substituted fused thiophene polymers (see Fong, H. H., supra.).

The solubility and solid state packing of these semiconductor polymers of formulas 4 and 5 in FIG. 7 can be modified using the disclosed flexible synthetic method to vary the length of alkyl side chain $R_1$, but also to vary the length of alkyl side chain $R_2$.

A potential high mobility polymer of formula 4a in FIG. 8 was synthesized and characterized. Modeling results indicated that that the polymer of formula 4a should have superior mobility and superior stability compared to our prior high performance polymer, P2TDC17FT4. A 69 nm red shift from the solution maximum absorption to the solid-state maximum absorption of this polymer suggested that this polymer is likely a high performance OTFT.

Figure 9:
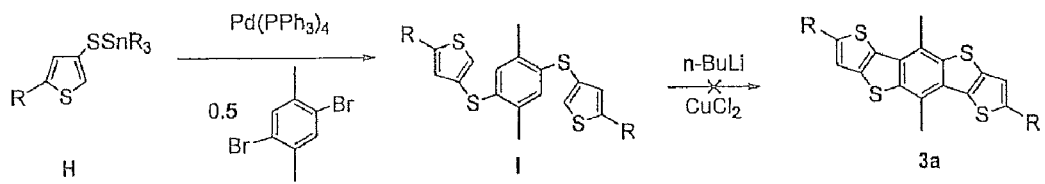
Figure 10:
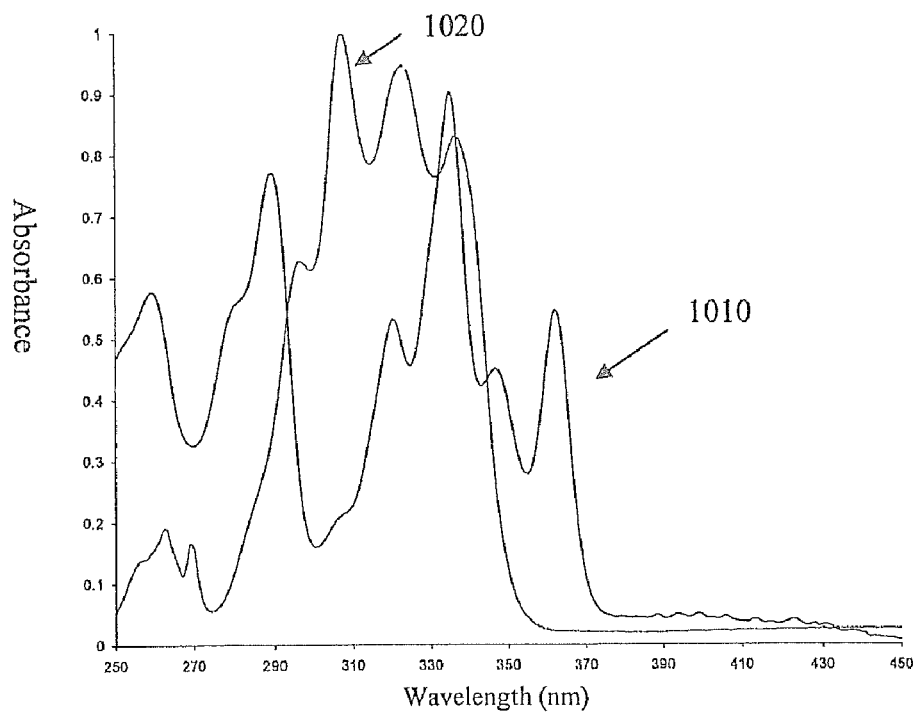
FIG. 10 shows example UV-vis solution spectra for a compound of FIG. 6 of the formula 2a having β-, β'-$C_{17}H_{35}$ substituents, and the known DC17FT4 having β-, β'-$C_{17}H_{35}$ substituents.

In embodiments, the disclosure provides methods to make α-, α'-un-substituted five-ring fused hetero aromatic compounds having $C_2$ symmetry (FIG. 4). In embodiments, the disclosure also provides methods to make their corresponding semiconducting polymers of formulas 4 and 5 (FIG. 7). These organic semiconductor polymers have utility in organic electronic devices. A recent publication highlighted the importance of $C_2$ symmetry in the design of high performance organic thin film transistors (He, M., et. al., "Importance of $C_2$ Symmetry for the Device Performance of a Newly Synthesized Family of Fused-Ring Thiophenes," *J. Chem. Materials*, (2010), 22(9), 2770-2779; see also Anthony, supra.). Accordingly, the presently disclosed five-ring fused hetero-aromatic compounds of formula 2 in FIG. 4 were designed and prepared having $C_2$ symmetry. Compound 2a of FIG. 6 can be expected to have higher mobility than that of DC17FT4 since literature examples indicate that with the same number of fused rings, the substitution of thiophene rings by phenyl rings in fused aromatics increases mobility significantly (Anthony, supra). Since the compound of formula 2a has one more ring (i.e., an additional aromatic for a total of five fused rings) than DC17FT4, it is expected to be more highly conjugated than DC17FT4. This expectation was supported by comparing their respective UV-vis spectra (FIG. 10). While others have been interested in synthesizing this class of symmetric five-ring fused heteroaromatics (Kastler, M., et al., "High performance solution processible semiconductor based on dithieno[2,3-d:2',3'-d']benzo[1,2-b:4,5-b'] dithiophene," WO 2010000670), there has been no reported synthesis of these α-, α'-un-substituted five-ring fused heteroaromatics of the formula 2 in FIG. 4. An initial attempted synthetic route to these α-, α'-alkyl substituted five-ring fused heteroaromatics of formula 3a as shown in FIG. 9 protected the α-, α'-position by alkyl chains to presumably facilitate the formation of two thiophene rings in the last ring closure step. However, several attempts to accomplish the final ring closure step showed that the target compound of formula 3a was either not formed or formed only as a minor product in less than about 10% yield in an inseparable crude mixture. Since the final ring closure reaction shown in FIG. 9 was unsuccessful, it was surmised that the construction of this α-, α'-un-substituted five-ring fused hetero aromatic might be accomplished from inside-out. That is, the interior three fused ring including phenyl ring could be constructed first, and then the two peripheral fused thiophene rings could be added. The general synthetic route using this approach is shown in FIG. 4. Compound of the formula 2a was prepared according to the route shown in FIG. 6. A pure compound of the formula 2a was obtained in an overall isolated yield of about 15%. With these α-, α'-un-substituted five-ring fused hetero aromatic compounds available, a known procedure of bromination using NBS of the compound of formula 2a to form the polymer precursor of formula 3 (step 1 in FIG. 7) should be successful (Fong, H.-H., "Tetrathienoacene Copolymers As High Mobility, Soluble Organic Semiconductors," *J. Am. Chem. Soc.*, (2008), 130(40), 13202-13203). Stille Coupling of precursor structure 3 with a di-tin compound (step 2 in FIG. 7) should readily form the desired semiconductor polymers containing the α-, α'-un-substituted five-ring fused heteroaromatics of formulas 4 and 5. By using this approach it was possible to prepare and characterize a potential high mobility polymer of the formula 4a shown in FIG. 8. Modeling studies indicated that the polymer of the formula 4a should have better mobility and thermal stability compared to our prior high performance polymer, P2TDCXFT4, as indicated by the Hole Reorganization Energy based on the repeat unit of both polymers. The structures of different fused aromatics were ranked from the lowest Hole Reorganization Energy (the highest mobility) to the highest Hole Reorganization Energy (the lowest mobility) in the Marcus model discussed below. These modeling results showed that Model Compound 9 for polymer 4a in the accompanying FIG. 14 Table 1 has a lower Hole Reorganization Energy than Model Compound 19 for our prior high performance polymer, P2TDCXFT4. The results suggest that the polymer of formula 4a should have a better mobility than our prior high performance polymer, P2TDCXFT4. The slightly lower Hole Reorganization Energy in Model Compound 9 than that of Model Compound 10 indicates the importance of the $C_2$ symmetry.

Figure 11:
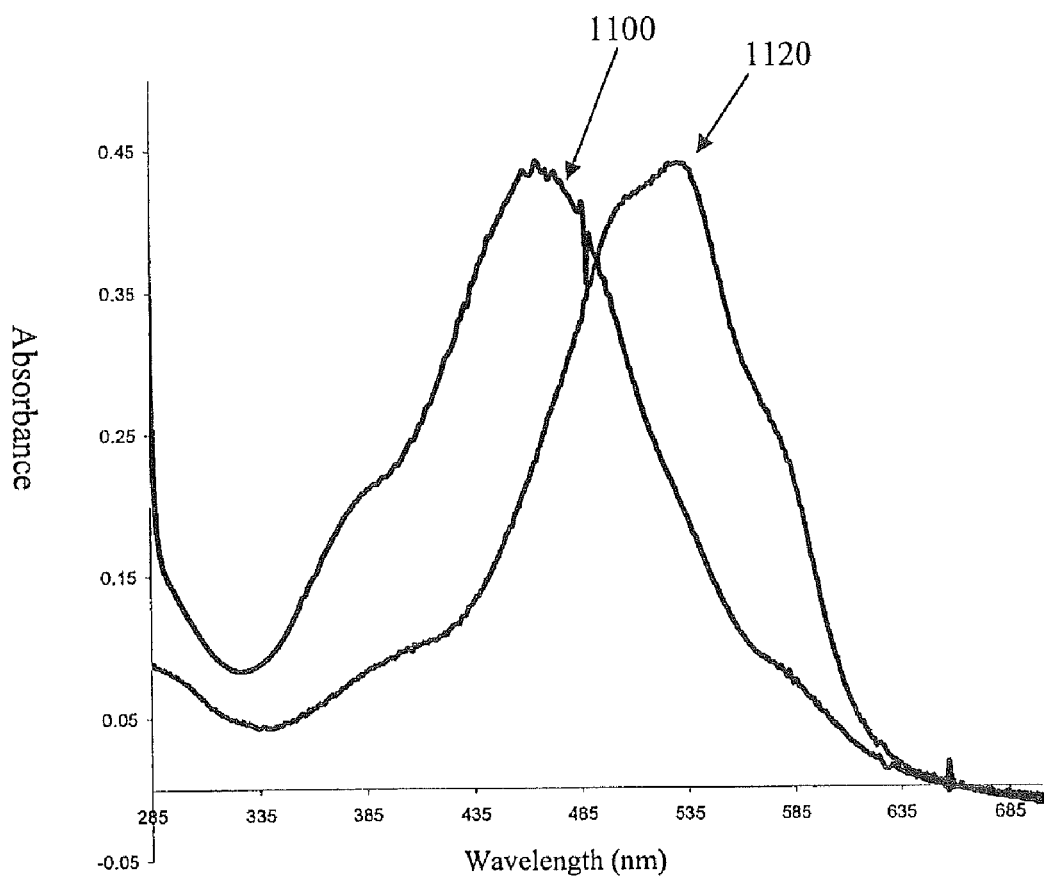
FIG. 11 shows examples of solution and solid UV-vis absorption spectra of the semiconducting polymer of formula 4a in FIG. 8.

FIG. 10 shows exemplary UV-vis spectra for compounds of FIG. 8 of the formula 2a: DC17PhFT2FT2 (1010) (solid line) having an β-, β'-$C_{17}H_{35}$ substituents of the formula:

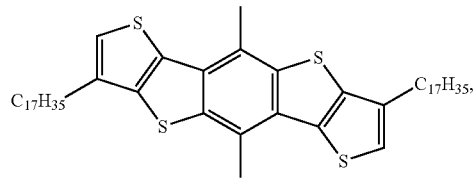

and the known DC17FT4 (1020) (dotted line) having an β-, β'-$C_{17}H_{35}$ substituents of the formula:

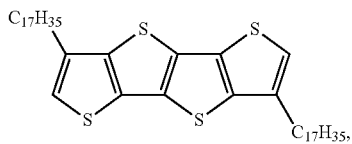

both measured in $CH_2Cl_2$. The shift in wavelength indicates that compound 2a (1010) has greater conjugation than DC17FT4 (1020) attributable to the added center fused phenyl ring. FIG. 11 shows examples of solution (1100) and solid (1120) UV-vis absorption spectra of the semiconducting polymer of formula 4a in FIG. 8. The observed red shift of about 69 nm from the solution maximum absorption to the solid-state maximum absorption for this polymer indicates that this polymer is most likely a high performance OTFT.

In embodiments, the disclosure provides a compound of the formulas 2, 2', 3 or 3',

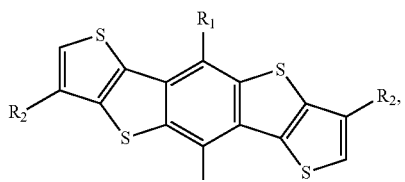

2

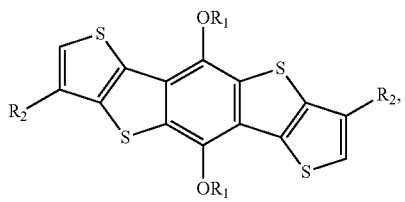

2'

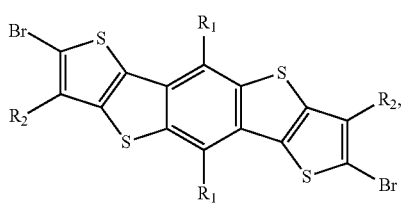

3

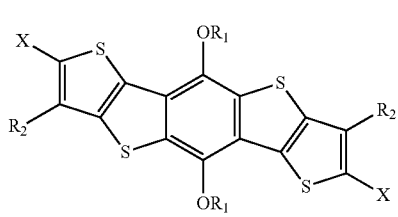

3' where $R_1$ and $R_2$ are independently selected from hydrogen, and a substituted or unsubstituted, branched or unbranched, ($C_{1-40}$) alkyl, or a salt thereof, or mixtures thereof.

The compound of the formula 2, 2', 3, or 3' can be, for example,

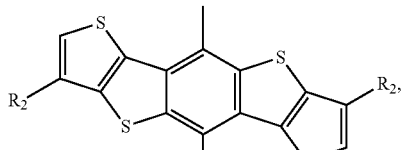

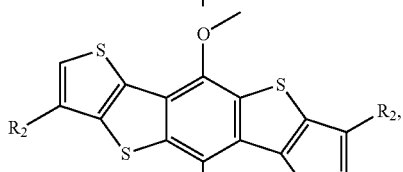

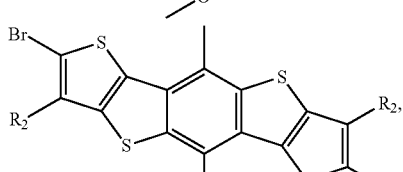

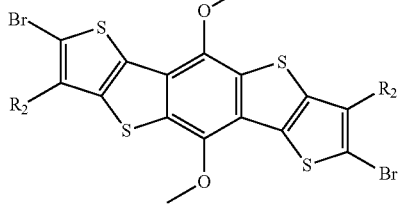

or a salt thereof, or mixtures thereof.

The compound of the formulas 2a, or 2b can be, for example:

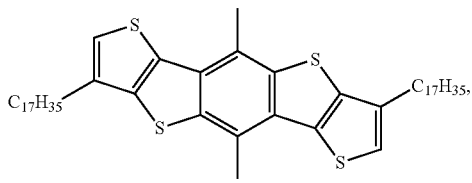

2a

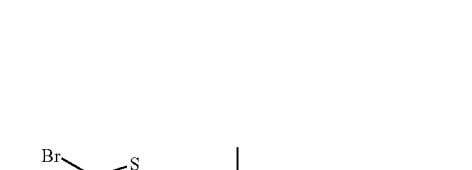

2b or a salt thereof, or mixtures thereof.

In embodiments, the disclosure provides a polymer of the formula 4, 4', 5, or 5',

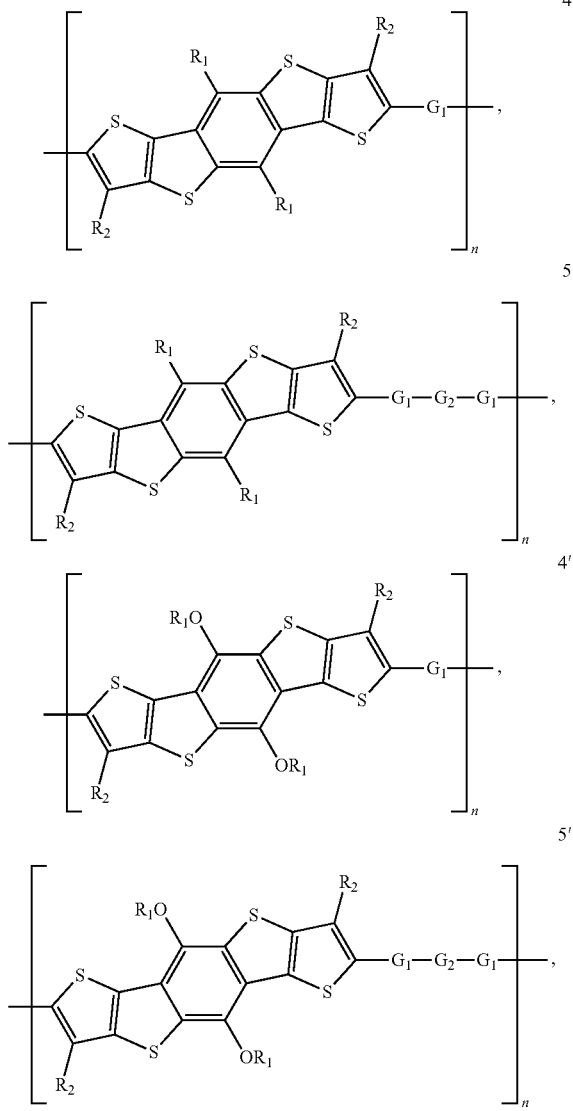

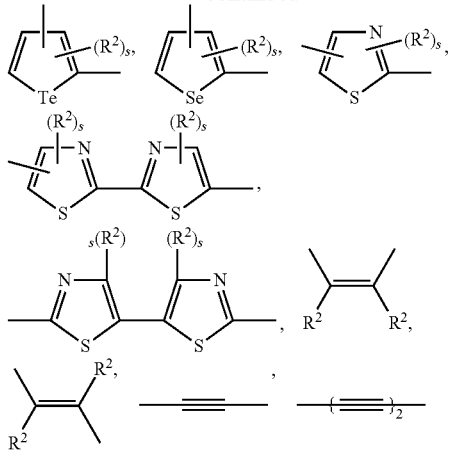

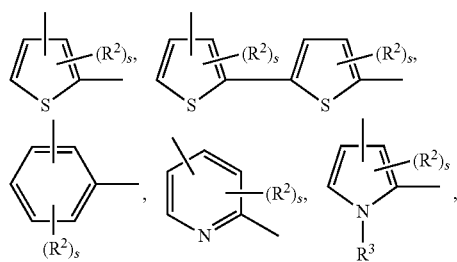

or a salt thereof, or mixtures thereof, where, for example, n can be an integer from about 3 to about 30, $R_1$ and $R_2$ can be independently selected from hydrogen, and a substituted or unsubstituted, branched or unbranched, $(C_{1-40})$ alkyl, $G_1$ and $G_2$ are divalent, substituted or unsubstituted, aromatic or heteroaromatic groups and can be each independently selected from, for example, or like groups, and combinations thereof, where $R^2$ can be independently selected from hydrogen, and a substituted or unsubstituted, branched or unbranched, $(C_{1-20})$ alkyl, and s is an integer of 0 to from 4.

The polymer of the formula 4, 4', 5, or 5', can be, for example,

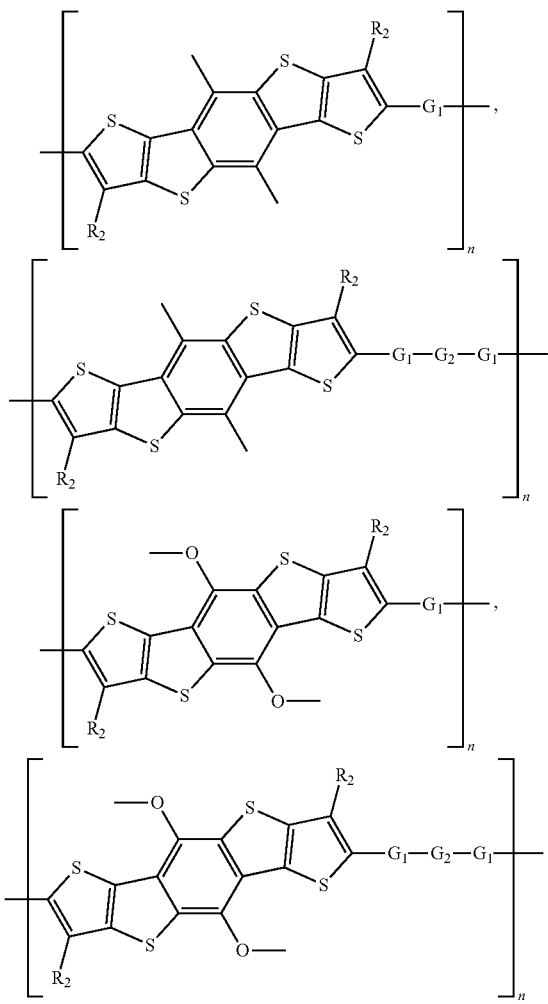

where n, R, $R_1$, $R_2$, $R_2$, $G_1$, and $G_2$ are as defined herein, or a salt thereof, or mixtures thereof.

The polymer of the formula 4a can be, for example,

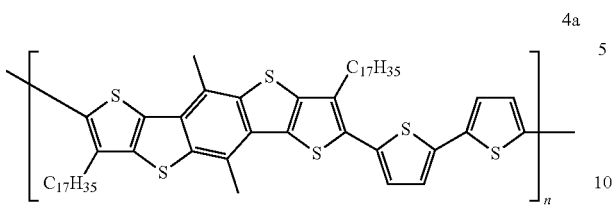
4a where n can be an integer from about 3 to about 30, or a salt thereof, or mixtures thereof.

In embodiments, the polymer of the formula 4a can have a mobility of, for example, from about 0.0192 to about 0.0772 $cm^2/V \cdot s$, including intermediate values and ranges.

In embodiments, the disclosure provides a method of making the compound of the formula 2, 2', 3 or 3', or a salt thereof, or mixtures thereof, comprising:

contacting a compound of the formula:

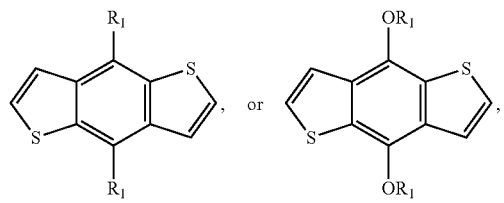

and at least two equivalents of a dihalogen or other suitable halogenation reagent, such as NBS, to respectively provide a compound of the formula:

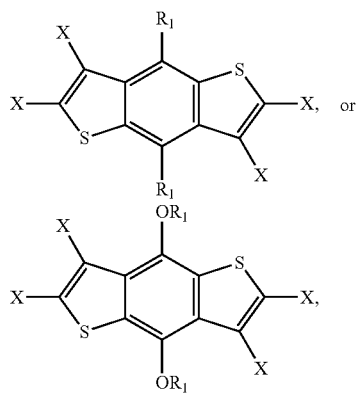

where X is halogen;

α, α'-diacylating the resulting halogenated product to respectively provide a compound of the formula:

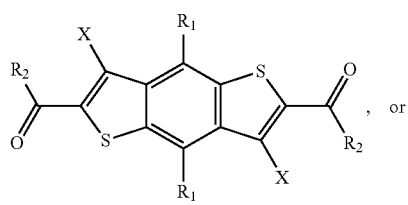

-continued

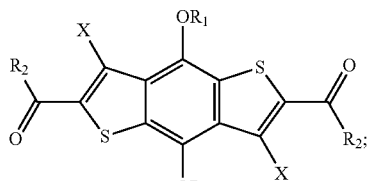

bis-annulating the resulting diacylated product with a β-thiol acetate ester to respectively provide a five-ring core compound of the formula:

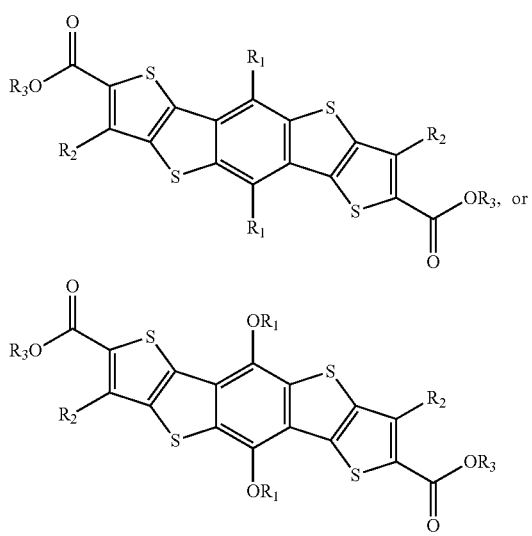

where —$R_3$ is $(C_{1-4})$alkyl;

hydrolyzing the resulting diester to respectively provide a diacid compound of the formula:

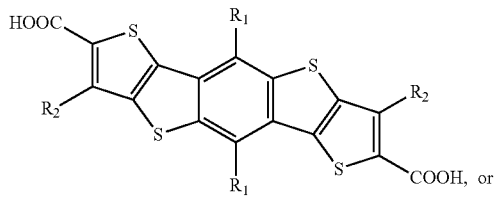

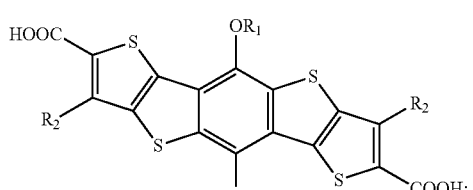

decarboxylating the resulting diacid to respectively provide an α, α'-unsubstituted compound of the formula 2 or 2':

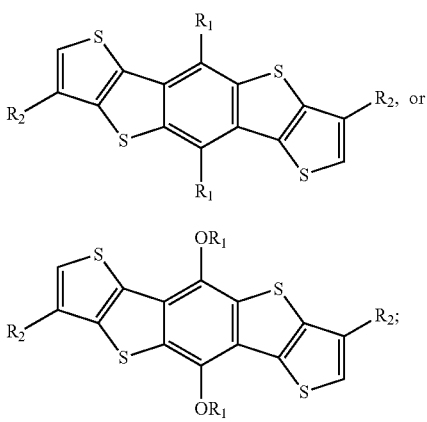

and contacting the compound of the formula 2 or 2' with a dihalogen to respectively provide a compound of the formula 3 or 3':

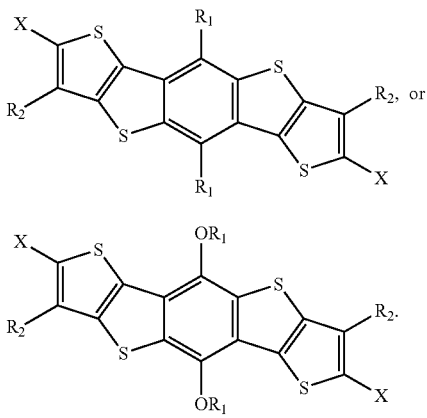

In embodiments, the α, α'-diacylating can alternatively be accomplished in two steps with an aldehyde equivalent to provide an intermediate of the formula:

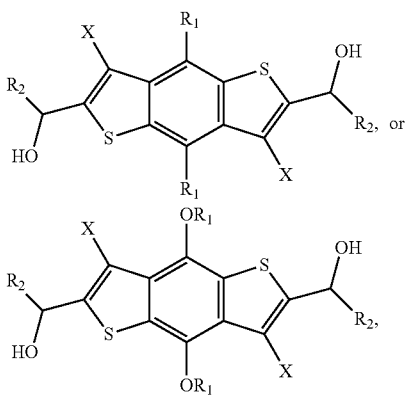

followed by oxidation instead of directly reacting with an acyl halide.

In embodiments, the disclosure provides a method of making a polymer of the abovementioned formulas 4 or 5, comprising for example:

contacting the dihalogen compound of formula 3:

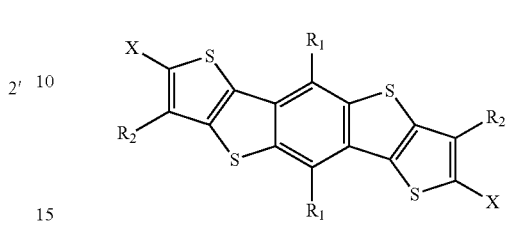

where X is halogen, with a di-tin compound of the formula $(R)_3Sn-G_1-Sn(R)_3$ or of the formula $(R)_3Sn-G_1-G_2-G_1-Sn(R)_3$ to respectively form a compound of the formulas 4 or 5:

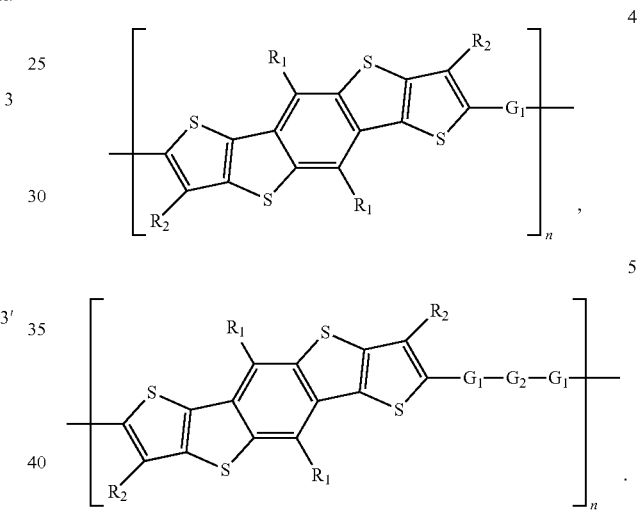

The dihalogen compound of formula 3 can be of the formula 2b:

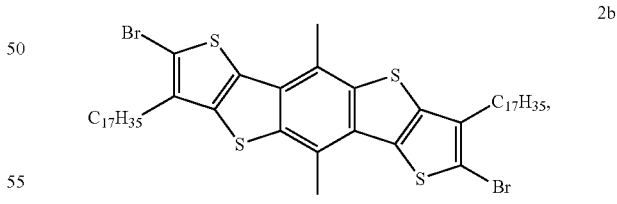

$(R)_3Sn-G_1-Sn(R)_3$ can be, for example, a bis-thiophene of the formula:

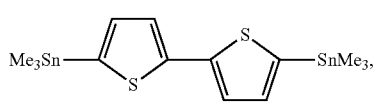

and
the polymer of the formula 4 can be of the specific formula 4a:

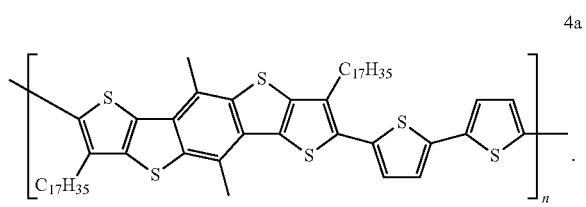

4a

In embodiments, the disclosure provides a device comprising at least one polymer of the formulas 4 or 5:

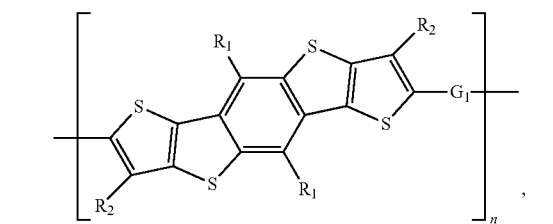

4

,

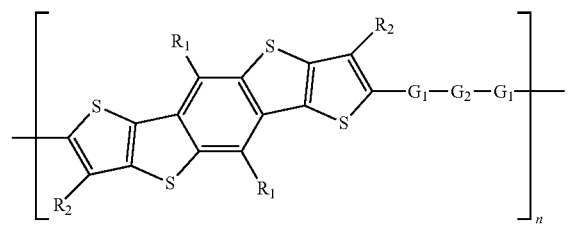

5

.

where $R_1$ can be, for example, $CH_3$, $R_2$ can be, for example, $C_{17}H_{35}$, $G_1$ and $G_2$ can be, for example, independently selected from -(thiophene)-, -(thiophene)$_2$-, -{(beta-$C_{17}$-substituted-thiophene), or -{(beta-$C_{17}$-substituted-thiophene)$_2$- and n is 5 to 20. In embodiments, $R_1$ can alternatively be —$OR_1$ as defined herein.

Molecular Design: Marcus Model

Charge transport properties depend on the degree of ordering of the π system or molecular ordering in the solid state as well as the density of chemical impurities, structural defects such as grain size and dislocations, or combinations thereof (see Garnier, F., et al., *Science* (1994) 265, 1684; Katz, H. E., *J. Mater. Chem.*, (1997) 7, 369; and Horowitz, G., *Adv. Mater.* (1998) 10, 365). At the electronic level, two of the more significant factors that control transport properties in organic conjugated materials are the interchain transfer integral β, and the reorganization energy λ. The transfer integral expresses the ease of transfer of a charge between interacting chains. The reorganization energy term describes the strength of the electron-phonon coupling. It is proportional to the geometric relaxation energy of the charged molecule over the individual neutral unit. In the context of semi-classical electron-transfer theory, the electron-transfer (hopping) rate can be expressed by Eq. (1) from Marcus theory in simplified terms as:

$$k_{et} = \frac{4\pi^2}{h} \frac{1}{\sqrt{4\pi k_B \lambda T}} \beta^2 e^{-\frac{\lambda}{4k_B T}} \quad (1)$$

where T is the temperature, λ is the reorganization energy, β is the transfer integral, and h and $k_B$ are the Planck and Boltzmann constants (see Marcus, R. A., *Rev. Mod. Phys.* (1993) 65, 599).

To characterize the relative influence of both parameters to the charge transport rate, replace Eq. (1) by a simpler expression (2):

$$k_{et}^{simple} = \frac{1}{\sqrt{\lambda}} \beta^2 e^{-\lambda} \quad (2)$$

Figure 12:
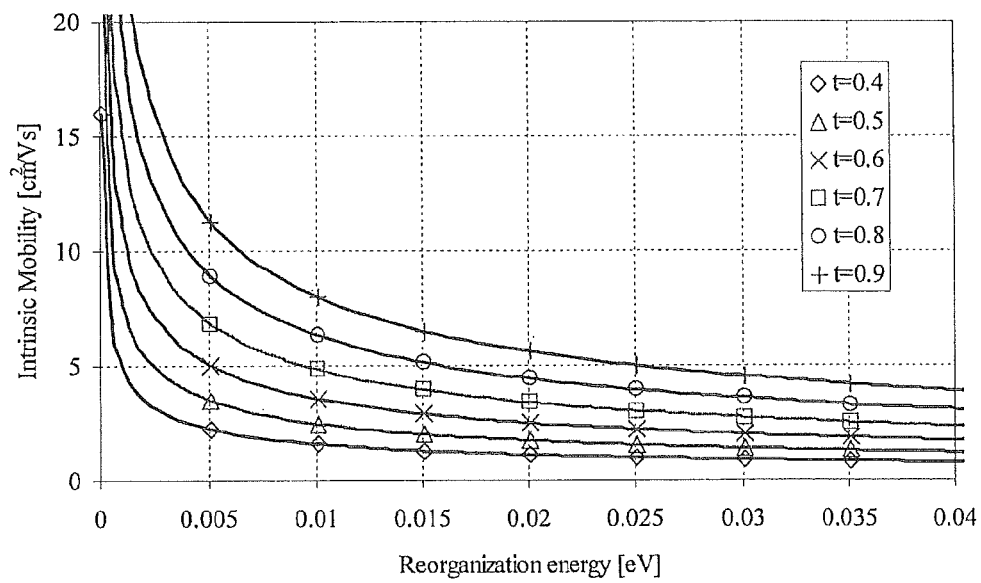
FIG. 12 illustrates reorganization energy and the transfer integral in the charge carrier mobility as deduced from modeling.

Eq. (2) describes a two variable function and allows assessment of the relative importance of the variables on the charge transfer rate, and hence mobility. The results in FIG. 12 depict how mobility varies as a function of the reorganization energy when five different values of the transfer integral are considered (i.e., calculated mobility (μ) over a transfer integral range from about 0.4 eV to about 2 eV). These are very realistic transfer integral values for a small molecule organic semiconductor. Deng calculated the transfer integral for pentacene with herringbone packing (Deng, W.-Q., et al., *J. Phys. Chem. B*, (2004), 108, 8614-8621). Their results of calculated mobility using Eq. (1) yielded reasonable agreement with the mobilities measured for a single crystal. The maximal values of the transfer integrals for different directions in crystalline pentacene were between 0.2 eV and 0.32 eV. A wider range was used in the present calculations to include optimal cases and beyond. From FIG. 12, it is apparent that the difference in mobility for different transfer integrals is only significant for small values of the reorganization energy. A large increase in the transfer integral does not yield a significant variation in the mobility, unless the reorganization energies are small. This implies that any optimization of the mobility should start with the design of a molecule with very low reorganization energy.

Modeling Details

The reorganization energy includes two contributions that are associated with charge hopping. One is introduced by the geometric changes within the single molecule, and is denoted the internal part. The second one arises from the re-polarization changes of the surrounding medium. This last contribution will be neglected in the evaluation of the reorganization energy. Such an approximation is valid since no significant solvent reorganization occurs during the charge transfer in the condensed phase. The reorganization energy for hole transfer, as considered in Eq. (1), can be estimated by Eq. (3) as the sum of two parts:

$$\lambda = \lambda_0 + \lambda_+ = (E^*_0 - E_0) + (E^*_+ - E_+) \quad (3)$$

Figure 13:
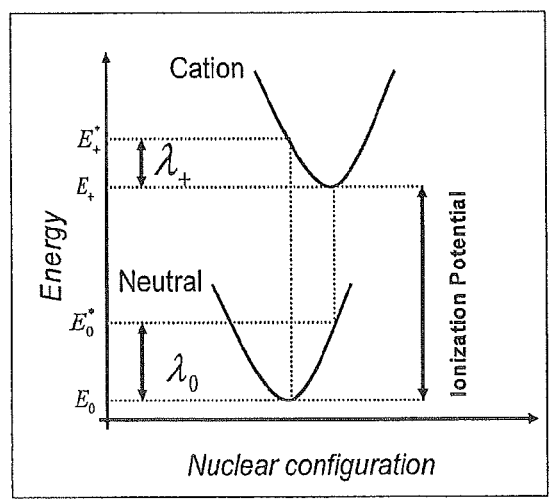
FIG. 13 illustrates the internal reorganization energy for hole transfer as a function of various internal reorganization components ($\lambda = \lambda_0 + \lambda_+$) and the ionization potential ($IP = E^*_+ - E$) as deduced from modeling.

FIG. 13 illustrates the calculation of the reorganization energy. For each molecule, the geometry is optimized using quantum mechanics for both neutral and ionic states. Consequently, the basic hopping step in a molecular wire is defined by four energies: $E_0$ and $E_+$ represent the energies of the neutral and cation species in their lowest energy geometries, respectively, while $E^*_0$ represents the energy of the neutral species having the optimized geometry of the cation and $E^*_+$ represents the energy of the cation species having the optimized geometry of the neutral species. The quantum mechanics calculations to determine these above mentioned quantities used the experimentally parameterized Hamiltonian PM6 implemented in VAMP® (Accelrys Software, Inc.) Pentacene was used as a reference to validate the Hole Reorganization Energy (RE) calculations. Experimental data for pentacene RE is about 0.12 eV, compared to 0.114 eV from VAMP. FIG. 14 lists in Table 1 the Hole Reorganization Energies for selected molecules having some structural resemblance to the repeat unit (Model Compound 9) of the polymer proposed as a good candidate for semiconductor applications and polymer (P2TDC13FT4, Model Compound 19 in Table 1). The monomer of the suggested polymer has a Hole Reorganization Energy of 0.199 eV compared to 0.243 eV for P2TDC13FT4. This corresponds to about an 18% improvement of the Hole Reorganization Energy.

Based upon other known and related compounds and polymers, the disclosed compounds and polymers are expected to have excellent organic semiconductor properties, such as increased thermal stability and oxidative stability, and increased ease of manufacture based on increased solubility and increased synthetic efficiency, such as fewer steps.

Advantages of the present preparative methods include, for example, the relatively straightforward path to a variety of new polymers and copolymers, especially those polymers having a core member having an aromatic center and at least two fused thiophenes annulated thereto. The di-tin fused thiophene monomer compounds are convenient to prepare because of their high crystallinity and solubility characteristics.

The disclosed preparative method can be extended to any fused aromatic di-tin monomer. The disclosed polymer or copolymer preparative methods can be extended to the synthesis of conjugated polymers having a like core including an aromatic center and at least two fused thiophenes annulated thereto.

EXAMPLES

The following examples serve to more fully describe the manner of using the above-described disclosure, and the best modes contemplated for carrying out various aspects of the disclosure. It is understood that these examples do not limit the scope of this disclosure, but rather are presented for illustrative purposes.

Experimental Details for Compound 2a (FIG. 6) and Polymer 4a (FIG. 8)

Example 1

Synthesis of Compound C

To a cloudy solution of compound B (0.28 g, 1.28 mmol) in mixed solvents of glacial HOAc (20 mL) and $CH_2Cl_2$ (4 mL) in darkness, 0.92 g (5.8 mmol) of $Br_2$ was added. The resulting mixture was stirred at room temperature for 3 days. Ice-cooled aqueous NaOH solution was added. Methylene chloride was then removed under reduced pressure to yield a solution containing a precipitate. The precipitate was then collected by filtration and washed successively with aqueous sodium carbonate solution, water, MeOH, and $CH_2Cl_2$. Compound C was collected as a greyish solid (0.68 g, 68%). $^1$H NMR (300 MHz, $d_8$-THF): δ 3.10 (s, 6H). GC/MS 535[M+].

Example 2

Synthesis of Compound D

To a cloudy solution of Compound C (1.60 g, 3.00 mmol) in anhydrous THF (55 mL) at −78° C., 2.66 mL of n-BuLi solution in hexane (2.25 M) was added dropwise under a nitrogen stream. This was stirred at −78° C. for about 3 hours until only a small amount of starting materials could be detected by GC/MS. To this mixture was quickly added a solution of 1.77 g (6.59 mmol) of n-$C_{17}H_{35}$CHO in anhydrous THF (8 mL). The solution was warmed to room temperature slowly overnight. It was then quenched with water. After removing THF, a light yellowish solid was collected by filtration and washed with water and then MeOH. Column chromatography of this solid yielded 1.05 gram (38%) of Compound D in about 90% purity. $^1$H NMR (300 MHz, $d_8$-THF): δ 5.14 (t, 2H), 3.11 (s, 6H), 1.82 (p, 4H), 1.70-1.43 (m, 64H), 0.89 (t, 6H).

Example 3

Synthesis of Compound E

To a solution of Compound D (5.83 g, 6.38 mmol) in refluxing acetone (200 mL), 19.1 mL of Jones Reagent was added dropwise. The resulting mixture was refluxed overnight. After cooling to about 25° C., a greenish precipitate was collected and it was mixed with hot aqueous 4N HCl solution and stirred for about 3 hours. This solid was further washed by acetone to yield 4.42 gram (75%) of Compound E. $^1$H NMR (300 MHz, $d_8$-THF): δ 3.22 (s, 6H), 3.17 (t, 4H), 1.79-1.42 (m, 60H), 0.89 (t, 6H).

Example 4

Synthesis of Compound F

To a stirred solution of Compound E (4.42 g, 4.86 mmol), $K_2CO_3$ (6.72 g, 48.6 mmol) and a catalytic amount of 18-crown-6 were added in DMF (50 mL). Ethyl mercaptoacetate 1.17 g (9.72 mmol) was added dropwise at 60-70° C. This mixture was stirred for three days. The mixture was then poured into water (400 mL) and the precipitate that formed was collected. The light yellowish precipitate was washed with water and then by MeOH (3.70 g, 80%). $^1$H NMR (300 MHz, $CD_2Cl_2$): δ 4.38 (q, 4H), 3.20 (t, 4H), 2.89 (s, 6H), 1.78 (p, 4H), 1.54-1.08 (m, 62H), 0.87 (t, 6H).

Example 5

Synthesis of Compound G

A solution of a mixture of Compound F (2.89 g, 3.04 mmol), LiOH (10% in water, 8.0 mL), THF (150 mL), water (10 mL), methanol (10 mL), and a catalytic amount of tetrabutyl ammonium iodide, was refluxed for about 24 hr. The mixture was then cooled to about 25° C. and most of THF and MeOH were removed. The resulting cloudy solution was then poured into water (50 mL). Aqueous hydrochloric acid (4N, 200 mL) was added to the aqueous residue. Solid was filtered and washed with water (3×300 mL). The light yellow solid of Compound G was washed with methanol (150 mL) and dried under vacuum overnight (2.64 g, 97%).

Example 6

Synthesis of Compound 2a

A mixture of Compound G (1.38 g, 1.54 mmol), $Cu_2O$ (0.100 g) and glycine (0.100 g) in tetraethyleneglycoldimethylether (40 mL) was heated to 220-230° C. in a flask fitted with drying tube. The reaction was terminated after 3 h. The hot reaction mixture was filtered as quickly as possible to remove the copper oxide or any other solid residue. The filtered solution was then cooled to about 25° C. and gave a pale yellow precipitate after short-path column chromatography purification. This pale yellowish solid was recrystallized from hexane to give the desired product, compound 2a (1.01 g, 81% yield) as a pale yellowish solid. $^1$H NMR (300 MHz, CD$_2$Cl$_2$): δ 7.23 (s, 2H), 2.92 (s, 6H), 2.83 (t, 4H), 1.84 (p, 4H), 1.56-1.10 (m, 56H), 0.89 (t, 6H).

Example 7

Synthesis of Compound 2b

To a cloudy solution of Compound 2a (0.75 g, 0.93 mmol) in 50 mL of CH$_2$Cl$_2$, a solution of 0.364 g (2.04 mmol) of NBS in 25 mL DMF was added. The resulting solution was stirred at about 25° C. for 2 days. This reaction was quenched by adding water (1 mL). Methylene chloride was removed under reduced pressure and 150 mL of water was added. A pale yellow precipitate formed and was collected, then washed with water and then MeOH. The material was recrystallized from toluene (20 mL) to give compound 2b (0.87 g, 97% yield) as a pale yellow solid. $^1$H NMR (300 MHz, CD$_2$Cl$_2$): δ 2.83 (s, 6H), 2.83 (t, 4H), 1.79 (p, 4H), 1.50-1.18 (m, 56H), 0.87 (t, 6H).

Example 8

Synthesis of Polymer 4a

Compound 2b (440.9 mg, 0.457 mmol) and 1,1'-[2,2'-bithiophene]-5,5'-diylbis[1,1,1-trimethylstannane] (225 mg, 0.457 mmol) were dissolved in toluene (25 mL) in a flask. Nitrogen was bubbled through this flask for a several minutes. Tetrakis (triphenylphosphine) palladium(0) (52.8 mg, 0.0457 mmol) was added to this mixture. The mixture was refluxed under nitrogen for 16 hr then poured into a methanol (300 mL) and concentrated hydrochloric acid (5 mL) solution and stirred for 16 hr at about 25° C. The precipitate was filtered and Soxhlet extracted sequentially with acetone and then hexane 24 h each. The collected dark-red polymer was dried in vacuum to yield 0.34 grams (76.6%) of polymer 4a ($\lambda_{max}$ in CH$_2$Cl$_2$ solution=465 nm, $\lambda_{max}$ in thin film=534 nm). GPC (1,2,4-trichlorobenzene) Mn=8,000, Mw=10,300; and PDI=1.28 relative to polystyrene standards.

Example 9

Device Fabrication and Characterization

All top-contact bottom-gate transistors using polymer 4a as an organic semiconducting channel were fabricated in air. Si<100> wafers were used as gate electrodes with silicon dioxide as the gate dielectric. OFET devices based on polymer 4a in 1,2-dichlorobenzene were fabricated on HMDS vapor treated Si/SiO$_2$ wafers. Polymer films were annealed at 150° C. Measured mobilities ranged from 0.0192 to 0.0772 cm$^2$/V s. On/off ratio ranged from $10^4$ to $10^5$.

The disclosure has been described with reference to various specific embodiments and techniques. However, it should be understood that many variations and modifications are possible while remaining within the scope of the disclosure.

What is claimed is:

1. A compound of the formulas 2a, or 2b:

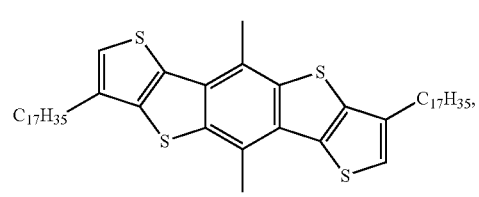

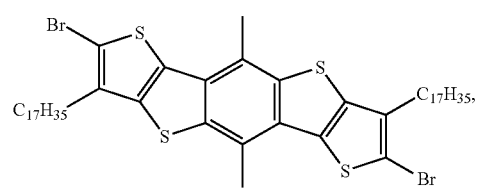

or a salt thereof, or mixtures thereof.

2. A method of making a compound of the formula 2, 2', 3, or 3'

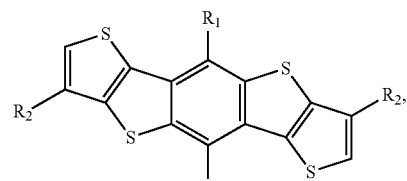

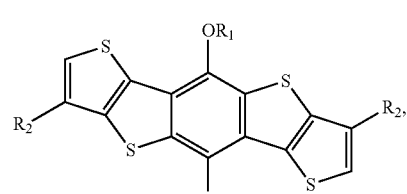

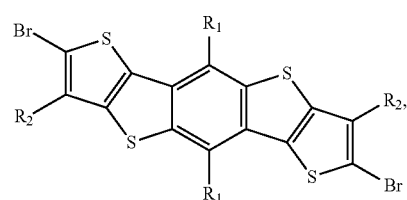

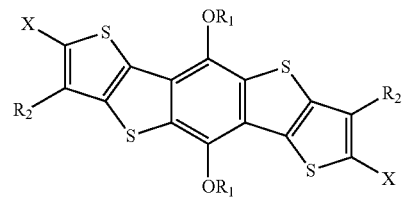

where

X is halogen

R$_1$ and R$_2$ are independently selected from hydrogen, and a substituted or unsubstituted, branched or unbranched, (C$_{1-40}$) alkyl, or a salt thereof, or mixtures thereof, comprising:

contacting a compound of the formula:

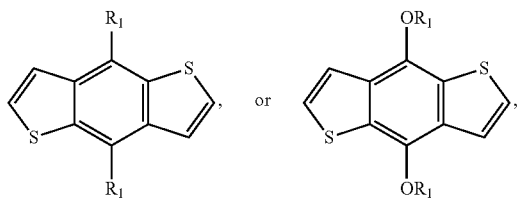

and a halogenating agent to respectively provide a compound of the formula:

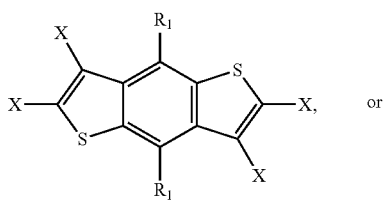

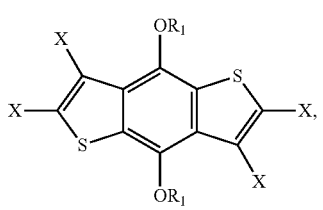

where X is halogen;

α, α'-diacylating the resulting halogenated product to respectively provide a compound of the formula:

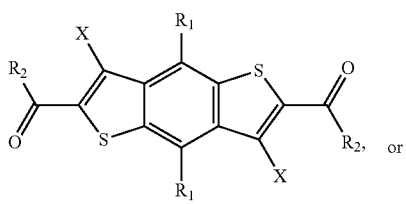

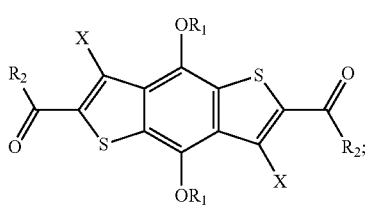

bis-annulating the resulting diacylated product with a β-thiol acetate ester to respectively provide a five-ring core compound of the formula:

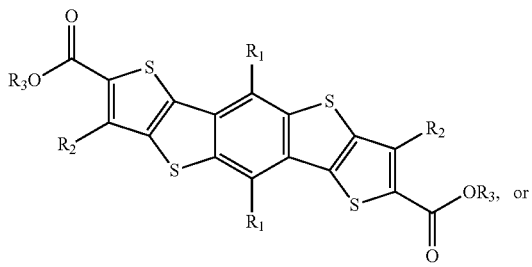

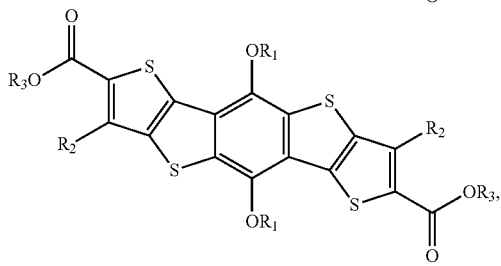

where —$R_3$ is $(C_{1-4})$alkyl;

hydrolyzing the resulting diester to respectively provide a diacid compound of the formula:

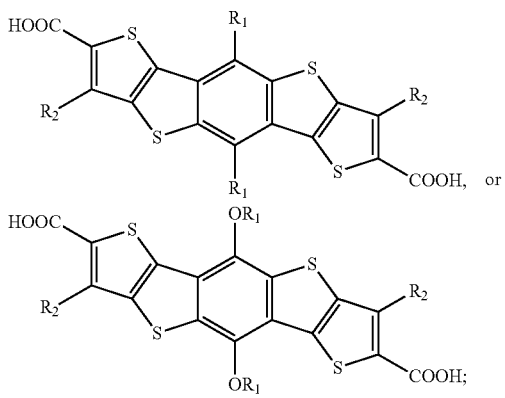

decarboxylating the resulting diacid to respectively provide an α, α'-unsubstituted compound of the formula 2 or 2':

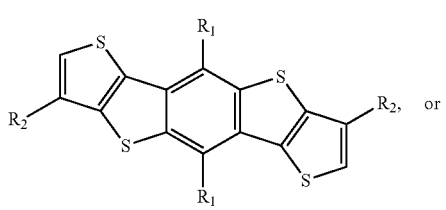

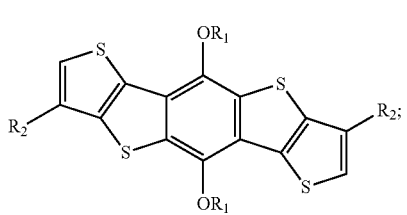

and
contacting the compound of the formula 2 or 2' with a halogenating agent to respectively provide a compound of the formula 3 or 3':
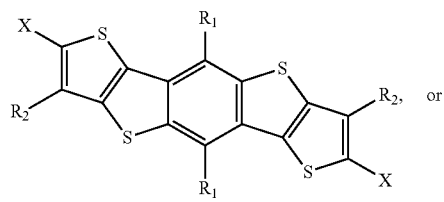
3
or
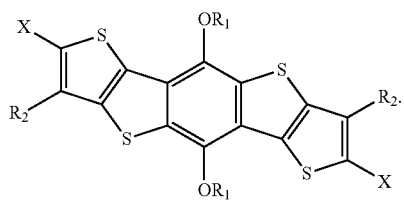
3'
* * * * *